(12) United States Patent
Modin et al.

(10) Patent No.: US 8,475,365 B2
(45) Date of Patent: Jul. 2, 2013

(54) HAND-HELD MEDICAL DEVICE PROTECTIVE SLEEVE

(76) Inventors: Rebecca L. Modin, Kearney, MO (US); Lisa A. Runion, Kearney, MO (US)

( * ) Notice: Subject to any disclaimer, the term of this patent is extended or adjusted under 35 U.S.C. 154(b) by 394 days.

(21) Appl. No.: 12/856,663

(22) Filed: Aug. 15, 2010

(65) Prior Publication Data

US 2011/0089175 A1    Apr. 21, 2011

Related U.S. Application Data

(60) Provisional application No. 61/279,151, filed on Oct. 15, 2009.

(51) Int. Cl.
*A61B 1/00* (2006.01)

(52) U.S. Cl.
USPC ........... 600/122; 600/121; 374/209; 206/363; 206/305

(58) Field of Classification Search
USPC .... 206/316.1, 316.2, 305, 320, 363; 150/154, 150/155, 161, 165; 383/209, 207; 374/158, 374/209; 600/121, 122
See application file for complete search history.

(56) References Cited

U.S. PATENT DOCUMENTS

| | | |
|---|---|---|
| 4,186,786 A | 2/1980 | Kirkpatrick |
| 4,446,967 A | 5/1984 | Halkyard |
| 4,576,283 A | 3/1986 | Fafournoux |
| D323,979 S | 2/1992 | Forman et al. |
| 5,339,959 A | 8/1994 | Cornwell |
| 5,480,302 A * | 1/1996 | Fife ................. 433/116 |
| 5,499,713 A * | 3/1996 | Huffer ............ 206/320 |
| 5,839,582 A | 11/1998 | Strong et al. |
| D402,543 S | 12/1998 | Thieman |
| 6,004,636 A | 12/1999 | Nicola et al. |
| D421,307 S | 2/2000 | Harmanoglu |
| 6,082,535 A * | 7/2000 | Mitchell ........... 206/320 |
| 6,305,536 B1 * | 10/2001 | Tanaka ............ 206/316.2 |
| 6,547,744 B1 * | 4/2003 | Pompei et al. ........ 600/549 |
| 6,550,966 B1 | 4/2003 | Saad et al. |
| 6,817,470 B1 * | 11/2004 | Goldberg ......... 206/320 |
| 6,983,845 B2 | 1/2006 | Shah et al. |
| 7,004,632 B2 | 2/2006 | Hamilton et al. |
| 7,011,213 B2 * | 3/2006 | Clark et al. ........ 206/438 |
| 7,147,105 B2 * | 12/2006 | Gammons ......... 206/320 |
| D557,148 S | 12/2007 | Kapinos, Sr. |
| 7,665,893 B2 * | 2/2010 | Buchalter ......... 374/158 |
| 7,987,979 B2 * | 8/2011 | Havens et al. ........ 206/320 |
| 2004/0231772 A1 * | 11/2004 | Leonard et al. ....... 150/161 |
| 2008/0190528 A1 * | 8/2008 | Steinberg ......... 150/165 |
| 2011/0089175 A1 * | 4/2011 | Modin et al. ........ 220/276 |
| 2012/0010468 A1 * | 1/2012 | Afridi ............. 600/121 |

\* cited by examiner

*Primary Examiner* — David Fidei
(74) *Attorney, Agent, or Firm* — Clifford Kraft

(57) ABSTRACT

A clear, sealable isolation sleeve for use in a medical environment especially with hand-held electronic devices, for the purpose of reducing the spread of infectious diseases. The sleeve offers an isolated containment for such hand-held medical devices while in patient proximity. The sleeve features a perforated tear zone for easy removal and disposal. Embodiments of the present invention can be manufactured from a clear material that allows the hand-held device to read bar codes through it, while also allowing the clinician to read displayed data and manipulate keypads on the device all while contained within the sleeve.

6 Claims, 4 Drawing Sheets

HAND-HELD MEDICAL DEVICE PROTECTIVE SLEEVE

This application is related to and claims priority from U.S. Provisional Patent application No. 61/279,151 filed Aug. 15, 2009. Application 61/279,151 is hereby incorporated by reference.

BACKGROUND

1. Field of the Invention

The present invention relates generally to protective covers and more particularly to protective covers for hand-held medical devices. Medical devices, when used in healthcare facilities, are subject to the spread of infectious diseases. Protective covers prevent this.

2. Description of the Prior Art

Infectious diseases that can be spread by contact with contaminated devices include nosocomial infections which are hospital-acquired infections where patients are infected with an organism as a result of contaminated hospital staff and/or surfaces. Nosocomial infections account for longer hospital stays, re-admissions due to newly acquired diseases, disfigurements and/or death. Organisms such as *Clostridium difficile*, Methicillin-resistant *Staphylococcus Aureus* (MRSA) are of utmost concern. These organisms or their spores are transferred from patient to patient via contaminated work surfaces, improper hand hygiene of hospital staff, or transferred on surfaces of medical equipment and instrumentation. The spores are highly resistant to cleaning and disinfection. Currently, no products are EPA-registered or in the prior art specifically for inactivating *C. difficile* spores.

Hand-held electronic medical devices are widely used in the healthcare industry. They include point-of-care blood analyzers, electronic patient identification devices, medication administration devices, personal data devices, and scanners. These are carried from one patient's room to another coming in contact with numerous candidates for potential infections. When not properly disinfected, they serve as a vector for infectious microorganisms. They pose a risk due to their design and intent of use. While they are designed for rapid recovery of data and multi-patient use, their design poses a problem of how to properly and rapidly disinfect their surfaces since they contain many crevices and surfaces that can house microorganisms. Also hand-held medical devices, being electronic, are not designed for total or even partial submersion in chemical disinfectants. The surfaces can only be wiped clean with available disinfectant products. These chemical disinfectants rely on time vs. exposure to deactivate the microorganisms, and the disinfectant must come in direct contact with the microorganism for a sustained period to render the microorganisms harmless. Therefore, widely distributed disinfectant wipes such as Clorox™ Wipes and Sani-Wipes are not generally recommended for the porous surfaces of hand-held medical devices.

The Centers for Disease Control (CDC) has recommended that healthcare organizations increase the use of disposable products as a preventative measure to decrease the spread of infectious disease. The product of the present invention is intended to meet that recommendation.

It would be advantageous and create an ideal situation in which to utilize hand-held electronic medical devices and decrease patient cross-contamination if the device could be isolated in a closed environment while in use, avoiding direct or indirect patient contact with the medical device. The device could be encased in a protective sleeve while it is in use in a patient room and removed when the device is transported to a subsequent room. The sleeve could be properly disposed of according to infection control protocol, and a new sleeve could be applied. This would create an environment that would contain potentially harmful microorganisms, reducing the risk of patient-to-patient transmission.

REPRESENTATIVE PRIOR ART

U.S. Pat. No. 5,839,582, Self-vacuum storage bag: A pumping system that is incorporated into and made part of a flexible, airtight bag of the interlocking seal variety. A means of pumping out air and other gases after the bag is sealed, for complete elimination of air and other gases.

U.S. Pat. No. 6,550,966, Freezer Storage Bag: A reclosable, multi-bag freezer bag including an inner liner bag and an outer support bag. The inner liner bag is a thermoplastic . . . [and] has a mouth through which the interior of the inner liner bag is accessible, and is joined by a mouth seal to the throat of the support bag along the entire length of the mouth of the liner bag substantially enclosing an air space between facing walls of the inner liner bag and outer support bag. The outer support bag has a reclosable mouth seal to provide reclosable access to the interior of the liner bag through the outer bag while maintaining the enclosed air space between the inner and outer bags.

U.S. Pat. No. 6,983,845, Reclosable storage bag with user-deformable air vent: A reclosable storage bag which may include first and second sides having closed sides and an open top. Primary closure members may be provided proximate the top, with a secondary closure element being provided in one of the sides to enable gas to be evacuated from the bag after the primary closure members are closed. The secondary closure member may be user-deformable, and reclosable after the gas is evacuated.

U.S. Pat. No. 7,004,632, Ventable storage bag: A storage bag for food products with a venting structure to expel excess air trapped inside the bag after the bag has been closed or sealed. After the excess air is removed, the venting structure is covered and sealed to prevent air from re-entering the bag or other objects from entering the bag.

U.S. Pat. No. 4,186,786, Colored interlocking closure strips for a container: An interlocking closure device comprising two closure profiles operable for being interlocked continuously over a predetermined length features the closure profiles having different colors, to simplify the closing and opening of the container.

U.S. Pat. No. 4,576,283, Bag for vacuum-packaging of articles: A separately attached sheet and an auxiliary chamber within a bag for vacuum packaging. The auxiliary chamber is evacuated when the bag is manufactured. This chamber may be placed in communication with the interior of the bag, after the latter has been filled and sealed. Such communication is achieved by piercing or tearing the separately attached sheet, so that the residual air in the sealed bag expands into a greater volume in which it is isolated from the product in the bag.

U.S. Pat. No. 5,339,959, Disposable medical waste bag: A disposable medical waste bag with layers of polyethylene film and an open top and a seal at the bottom of the bag. The bag is sealed by closing off the top of the bag by twisting. After a twist is formed, it is bent over on itself and an adhesive tape on the outside of the bag is used to tape the twist to itself, thereby thoroughly sealing the bag. A normally-closed valve on the bag is removably engagable with a coupler that is used in conjunction with the hose of a central vacuum system of a medical facility such as a hospital. After the bag has been sealed, the central vacuum system vacuums excess air from the bag thereby substantially decreasing the size of the bag.

U.S. Pat. No. 4,446,967, Germicide sleeve for dental and medical instruments: A germicide sleeve for dental and medical instruments comprising a flexible non-permeable outer sleeve wall of plastic or the like, the sleeve being closed at one end, the inner wall lined with a compressible absorbent material such as foam rubber surrounding an elongated central cavity or bore which extends the length of the sleeve and opens at an open end thereof to receive the working portion of a dental or medical instrument therein, the absorbent material being impregnated with a germicide.

U.S. Pat. No. 6,004,636, Medical bag: An empty medical bag that is heat-sterilized and made of a matrix-phase polymer system. After heat sterilization, the inside surfaces do not adhere to each other.

D421,307, Specimen Bag: Ornamental design for a specimen bag.

D402,543, Waste bag: Ornamental design for a waste bag.

D557,148, Tamper-evident bag for medical storage: Ornamental design for a tamper-evident bag for medical storage.

D323,979, Tamper-evident, resealable bag: Design for tamper-evident, resealable bag.

SUMMARY OF THE INVENTION

The present invention relates to a clear, sealable isolation sleeve for use in a medical environment especially with hand-held electronic devices, for the purpose of reducing the spread of infectious diseases. The sleeve offers an isolated containment for such hand-held medical devices while in patient proximity. The sleeve features an easy way to seal the instrument in the sleeve and a perforated tear zone for easy removal of the instrument and disposal of the sleeve. Embodiments of the present invention can be manufactured from a clear material that allows the hand-held device to read bar codes through it, while also allowing the clinician to read displayed data and manipulate keypads on the device all while contained within the sleeve.

To use this invention, the user generally places the hand-held medical device in the opening of the sleeve. A tab is then removed to expose a self-adhesive flap or similar closure. This flap can then be folded over and adhered to the outer surface of the opposite wall enclosing the hand-held medical device in the protective sleeve. The then clinician uses the now-encased medical device as designed. When the clinician exits the patient's room, he or she pulls on the lower half of the sleeve, tearing it at the perforated score-line and removing the sleeve for proper disposal. A new sleeve is used each time a hand-held medical device is introduced into a patient room.

DESCRIPTION OF THE FIGURES

Attention is now directed to several illustrations to aid in understanding features of the present invention.

DESCRIPTION OF THE INVENTION

The present invention relates to a plastic or other transparent sleeve or bag that can be used in a hospital environment to enclose hand-held devices, especially hand-held electronic devices while in proximity to a particular patient or in a particular room. The sleeve or bag is a disposable that can be removed from the instrument in a safe way after use and disposed of by safe and accepted methods.

Figure 1:
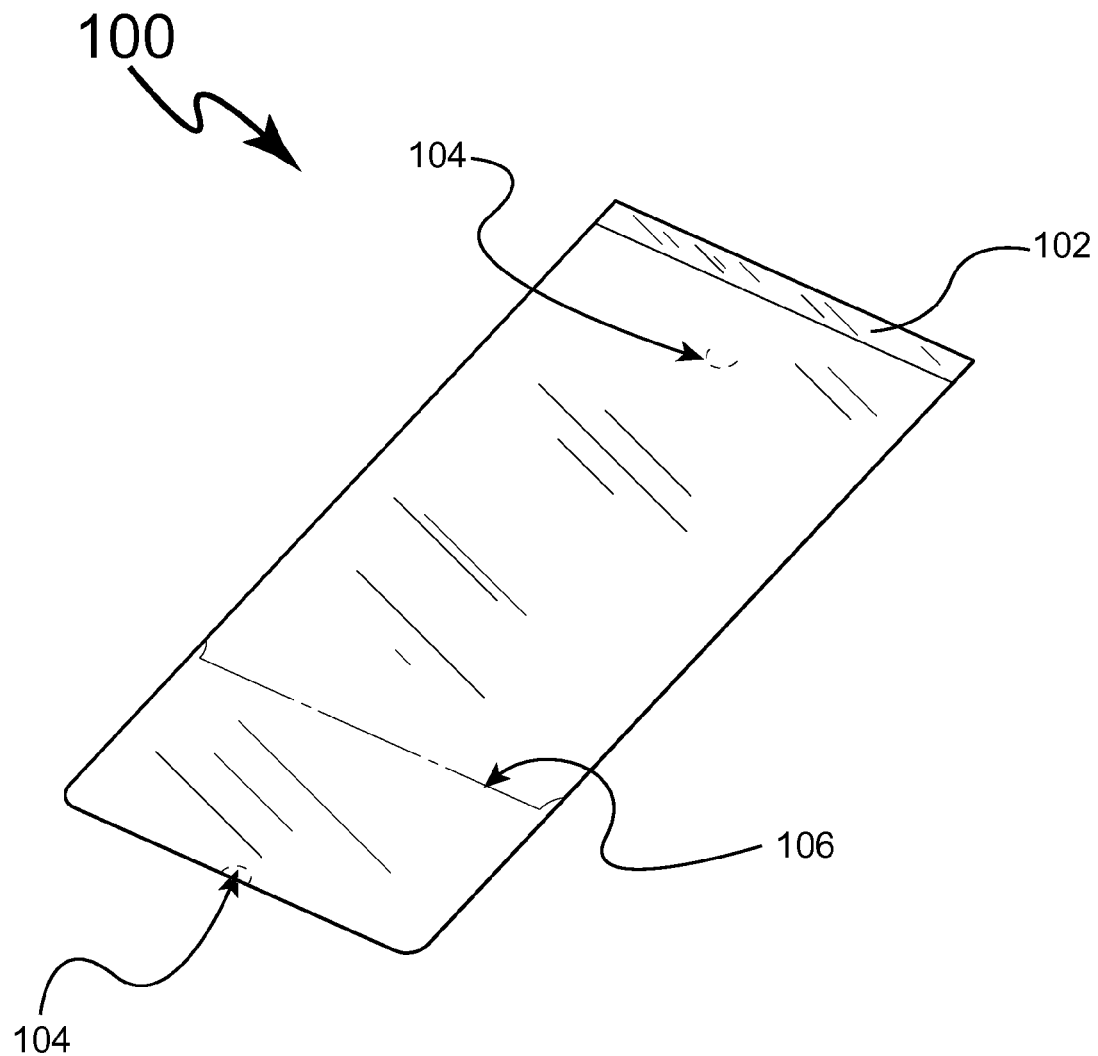
FIG. 1 is an isometric view of the embodiment (without the hand-held medical device enclosed)

Turning to FIG. 1 an embodiment of the present invention can be seen. A sleeve 100 is shown in its folded state before use. The sleeve has a peel-and-stick adhesive flap 102, typically two or more tear-open flaps 104 for stylus-pen access, and a tear-away perforation 106 located toward the end of the sleeve away from the flap. The perforation 106 can be typically located about ¼ of the length of the sleeve from the bottom end. Any location of the perforation 106 is within the scope of the present invention. The peel-and-stick adhesive flap 102 can be generally covered by a pull-away strip for protection. The device can be made of clear, FDA-approved polyurethane film or any other flexible, transparent material.

Figure 2:
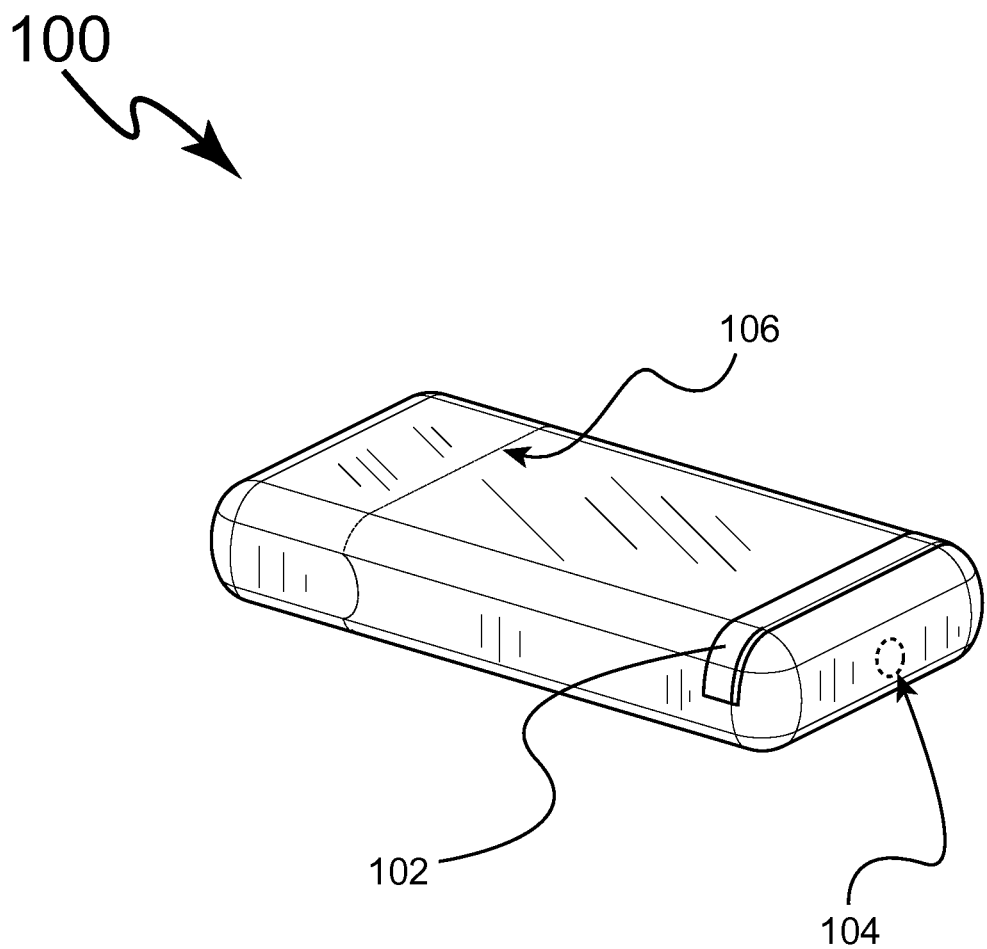
FIG. 2 is an isometric view of the embodiment showing the perforated, tear-open flap and the tear-open flaps for stylus-pen access (all in closed position)

FIG. 2 shows the embodiment of the sleeve 100 as it would appear enclosing a medical device and ready to be used. The adhesive flap 102 is shown folded over and adhered to the sleeve body. The tear-away perforation 106 is intact. Perforated tabs for stylus pens 104 are also intact.

Figure 3:
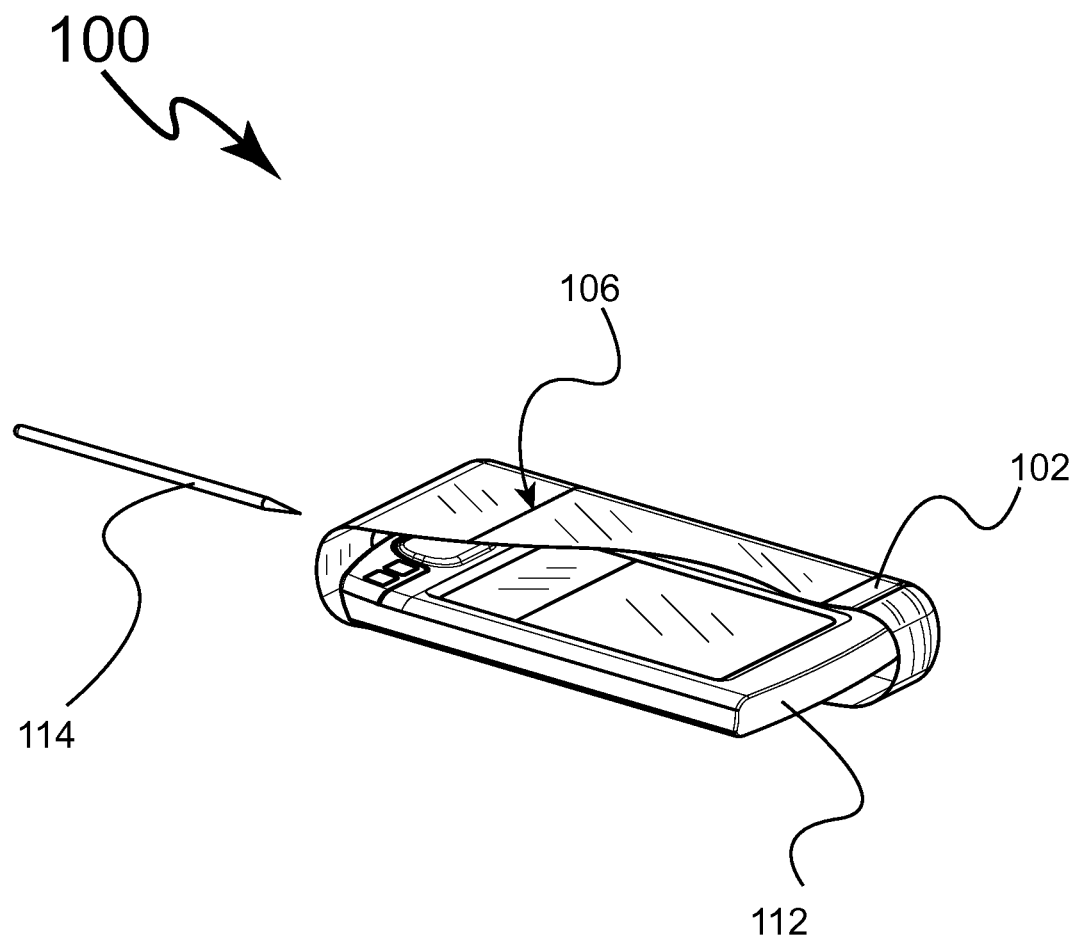
FIG. 3 is a cutaway view showing the embodiment with a hand-held medical device inside it

FIG. 3 shows a cutaway view of an embodiment of the invention containing a typical hand-held medical device 112. An example stylus pen 114 is shown unattached; the tear-away perforation 106 is still intact, and the adhesive flap 102 is shown folded over and enclosing the hand-held medical device 112.

Figure 4:
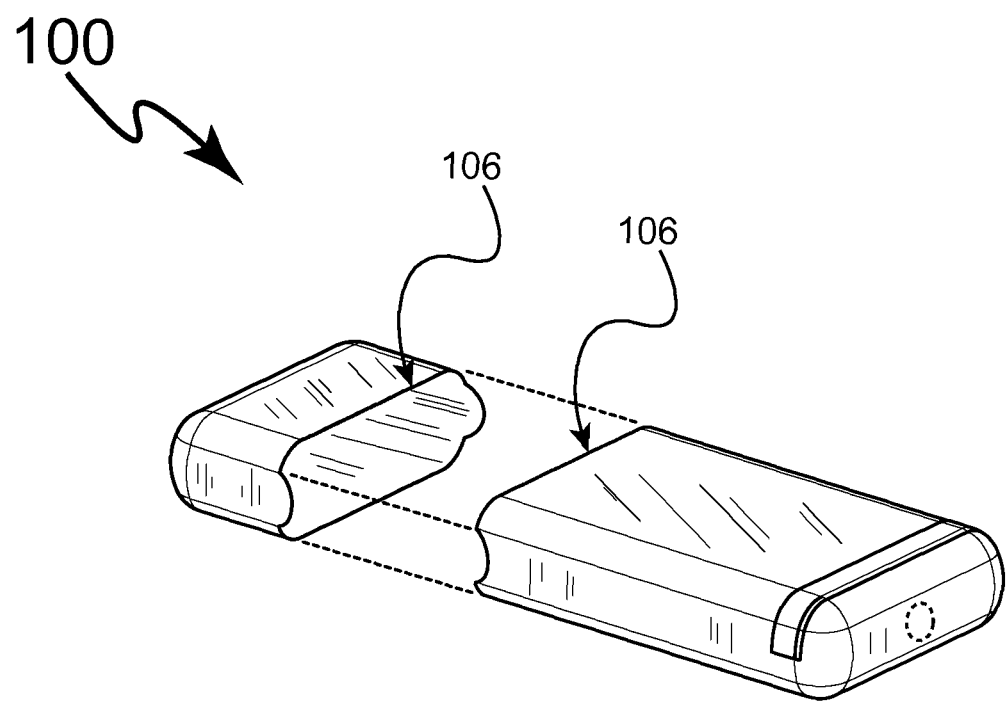
FIG. 4 is an isometric view showing the embodiment after it is torn open for removal of the hand-held medical device Several drawings and illustrations have been provided to aid in understanding the present invention. The scope of the present invention is not limited to what is shown in the figures.

In FIG. 4, the sleeve 100 is shown pulled apart at its perforation 106, and ready to be safely discarded.

Again, to use this invention, the clinician places the hand-held medical device in the opening of the sleeve 100. A tab is then removed to expose the self-adhesive flap 102 or similar closure. The hand-held device 112 is placed inside the sleeve 100, and adhesive flap 102 is folded over and adhered to the outer surface of the opposite wall enclosing the hand-held device 112 in the protective sleeve 100. The then clinician uses the now-encased medical device 112 as designed. When the clinician exits the patient's room, he or she pulls on the lower half of the sleeve, tearing it at the perforated score-line 106 and removing the sleeve 100 for proper disposal. A new sleeve is used each time the hand-held medical device 112 is introduced into a patient room.

The device of the present invention can be made from any strong partially transparent and flexible material with high-clarity FDA approved polyurethane being the preferred material. The construction can be from 2-ply urethane sealed together at a lower end. The device can be made in various sizes and shapes to fit different sized instruments.

The present invention can be used in any hospital-like environment including, but not limited to, actual hospitals, nursing homes, clinics, doctors' offices, assisted living facilities and any other facility where multiple patients are housed.

Several descriptions and drawings have been provided to illustrate features of the present invention and aid in their understanding. One with skill in the art will realize that numerous changes can be made without departing from the spirit of the invention. Each of these changes and variations is within the scope of the present invention.

We claim:

1. A method of preventing disease spread in a hospital-like environment comprising:

inserting a hand-held medical instrument into a generally rectangular sterile transparent plastic sleeve having generally flat top and bottom surfaces, said sleeve allowing viewing of bar codes and data from said medical instrument through the plastic, said sleeve also having a tear-open stylus pen access port on said generally flat top surface, and a closing flap at a first end, said closing flap having a peel-and-stick adhesive strip;

removing a pull-away strip from an adhesive coating on said adhesive strip;

folding said closing flap over said first end so that said adhesive coating contacts a surface of said sleeve closing said sleeve around the instrument;

using said instrument in proximity to a patient by reading bar codes or data through said plastic;

separating a part of said sleeve near a second end of the sleeve by pulling on a tab on said second end causing a perforation around said sleeve to tear open;

allowing said instrument to exit said sleeve;

disposing of said sleeve according to an infection control protocol.

2. The method of claim 1 wherein said sleeve is made from FDA approved, high-clarity polyurethane.

3. The method of claim 1 wherein said sleeve can be manufactured in a plurality of sizes and shapes to fit different hand-held instruments.

4. A method of preventing the spread of infectious diseases in a hospital-line environment comprising:

selecting a generally rectangular transparent plastic sleeve with generally flat top and bottom surfaces with a proximal end and a distal end, said sleeve open at said proximal end and closed at said distal end with a flap at the proximal end that can fold over and close the proximal end, said sleeve having a peel-and-stick adhesive tab running across one surface of said proximal end adapted so that when said flap is folded over closing the proximal end, the adhesive tab contacts an outer surface of said sleeve keeping the sleeve closed, said sleeve also having a tear-away perforation running laterally around said sleeve located nearer said distal end than said proximal end of the sleeve, said sleeve also having a tear-open stylus pen access port on said generally flat top surface inserting a hand-held medical instrument into said sleeve, said flap being folded over and adhesively attached a surface of said sleeve to close said sleeve around said instrument;

using said hand-held medical instrument by reading bar codes or data from said instrument through said plastic;

tearing said sleeve at said tear-away perforation to remove said instrument, wherein said sleeve can be disposed of according to an infection control protocol.

5. The method of claim 4 wherein said sleeve is made from FDA approved, high-clarity polyurethane.

6. The method of claim 4 wherein said sleeve can be manufactured in a plurality of sizes and shapes to fit different hand-held instruments.

* * * * *